United States Patent
Choi

Patent Number: 6,165,680
Date of Patent: Dec. 26, 2000

[54] DISSOLUTION INHIBITOR OF CHEMICALLY AMPLIFIED PHOTORESIST AND CHEMICALLY AMPLIFIED PHOTORESIST COMPOSITION CONTAINING THE SAME

[75] Inventor: Sang-jun Choi, Seoul, Rep. of Korea

[73] Assignee: Samsung Electronics Co., Ltd., Suwon, Rep. of Korea

[21] Appl. No.: 09/234,516

[22] Filed: Jan. 21, 1999

[30] Foreign Application Priority Data

May 20, 1998 [KR] Rep. of Korea ................. 98-18201

[51] Int. Cl.$^7$ ..................................................... G03F 7/004
[52] U.S. Cl. ......................... 430/270.1; 560/82; 430/914
[58] Field of Search ......................... 430/270.1, 914; 560/129, 190, 82

[56] References Cited

U.S. PATENT DOCUMENTS

| | | | |
|---|---|---|---|
| 4,491,628 | 1/1985 | Ito et al. | 430/176 |
| 5,035,979 | 7/1991 | Nguyen-Kim et al. | 430/270 |
| 5,508,025 | 4/1996 | Hoshino | 424/59 |
| 5,532,106 | 7/1996 | Frechet et al. | 430/191 |
| 5,609,989 | 3/1997 | Bantu et al. | 430/270.1 |
| 5,852,128 | 12/1998 | Padmanaban et al. | 525/328.8 |

FOREIGN PATENT DOCUMENTS

| | | |
|---|---|---|
| 381362 | 10/1931 | United Kingdom . |
| 561105 | 7/1941 | United Kingdom . |
| 653319 | 1/1948 | United Kingdom . |
| 923854 | 8/1959 | United Kingdom . |
| 970948 | 12/1961 | United Kingdom . |

OTHER PUBLICATIONS

Chemical Abstracts Registry File, Registry No. 2163–44–2.

Tohru Ushirogouchi et al.; "Dissolution Inhibitors for 193–NM Chemically Amplified Resists"; Jpn. J. Appl. Phys., Part 1 (1997), 36(12B), 7625–7631 Coden: JAPNDE; ISSN: 0021–4922 abstract only.

R Schwalm et al.; "Dissolution Inhibitors and Modulators for Chemical Amplification Resists"; J. Photopolym. Sci. Technol. (1990), 3(3), 347–354 Coden: JSTEEW Abstract only.

*Primary Examiner*—Janet Baxter
*Assistant Examiner*—Rosemary Ashton
*Attorney, Agent, or Firm*—Jones Volentine, LLC

[57] ABSTRACT

A dissolution inhibitor for use in a chemically amplified photoresist, and a chemically amplified photoresist composition containing the same are provided. The dissolution inhibitor is a compound in which an acid-labile di-alkylmalonate group is combined as a functional group with a $C_1$ to $C_{20}$ hydrocarbon. The chemically amplified photoresist composition containing the dissolution inhibitor has a high contrast and high thermal decomposition temperature, making it suitable for forming a fine pattern having excellent profile.

25 Claims, No Drawings

DISSOLUTION INHIBITOR OF CHEMICALLY AMPLIFIED PHOTORESIST AND CHEMICALLY AMPLIFIED PHOTORESIST COMPOSITION CONTAINING THE SAME

BACKGROUND OF THE INVENTION

1. Field of the Invention

The present invention relates to a material for forming a semiconductor device, and more particularly, to a dissolution inhibitor of a chemically amplified photoresist used in photolithography, and a chemically amplified photoresist composition containing the same.

2. Description of the Related Art

Current semiconductor chips are highly integrated and require complicated manufacturing processes, for example, photolithography processes that are capable of forming fine patterns in the range of 0.25 µm or less. Such fine patterns are formed using deep ultraviolet (UV) rays of 248 nm, which have a shorter wavelength than conventional g-line (436 nm) and I-line (365 nm) rays. However, when deep-UV rays are used, a smaller number of protons are transferred when a dose of the same energy as a conventional light source is irradiated. Therefore, a dose of much greater energy is required in order to transfer the same number of protons and obtain the same result as is achieved using conventional photolithography. To overcome this problem, a new material called "chemically amplified photoresist" has been introduced, which is highly sensitized to protons due to its improved photosensitivity, even if the deep-UV rays are irradiated at a similar dose to that used with conventional light source irradiation.

In general, the chemically amplified photoresist includes an acid-labile group which is easily subjected to acid hydrolysis by an acidic catalyst which functions as a dissolution inhibitor. The amplified photoresist also includes a photosensitive acid generator for generating protons H$^+$ (i.e., acid) by exposure to light. When the chemically amplified photoresist is exposed to light, acid is generated by the photosensitive acid generator. The dissolution inhibitor, which is bound to the backbone of the polymer, is hydrolyzed by the catalytic reaction of the generated acid, thereby changing the polarity (e.g., solubility) of the polymer. Acid hydrolysis of the polymer by the diffusion of acid then occurs, resulting in a pattern that has a higher transparency.

Thus, contrast, (i.e., an index for representing the difference in solubility of a chemically amplified photoresist before and after the exposure to light), is determined by the acid-labile group bound to the backbone of the polymer.

U.S. Pat. No. 4,491,628 discloses a chemically amplified photoresist containing a polymer and using a t-butoxycarbonyl (t-BOC) as an acid-labile group. However, such a chemically amplified photoresist has a thermal decomposition temperature (Td) lower than its glass transition temperature (Tg). Thus, if the photoresist is baked to a temperature that is above the glass transition temperature before exposure to light, in order to vaporize unwanted organic solvent and make the photoresist film hard, the photoresist decomposes. On the other hand, if the pre-baking temperature is low enough to prevent thermal decomposition, airborne contaminants can be absorbed into the surface of the exposed photoresist film, thereby preventing a catalytic reaction by the acid. This results in a pattern having an inferior profile, such as a T-top profile. T-top profiles are the result of airborne contaminants that are absorbed into the photoresist film surface which neutralize the acid that is generated by the photoresist upon exposure to light. As a result, some portions of the exposed photoresist do not undergo acid hydrolysis and thus remain insoluble. The insoluble portions of the photoresist are not developed by the developer and result in T-top profiles.

SUMMARY OF THE INVENTION

To solve the above problems, it is an objective of the present invention to provide a dissolution inhibitor which is composed of a chemically amplified photoresist composition together with a photosensitive polymer. The dissolution inhibitor increases the contrast of the chemically amplified photoresist composition and provides excellent thermal characteristics.

It is another objective of the present invention to provide a chemically amplified photoresist composition which has excellent thermal characteristics as well high contrast which results in a high resolution pattern.

To achieve the first objective, there is provided a dissolution inhibitor for use in a chemically amplified photoresist, in which an acid-labile di-alkylmalonate group is combined as a functional group with a $C_1$ to $C_{20}$ hydrocarbon.

Preferably, the di-alkylmalonate group is one selected from the group comprising of di-t-butylmalonate, di-tetrahydropyranyl malonate and di-trimethylsilylmalonate, and the $C_1$ to $C_{20}$ hydrocarbon is one selected from the group comprising cyclohexane, dimethylenecyclohexane, xylene and methyinaphthalene.

In a second objective, there is provided a chemically amplified photoresist composition composed of a photosensitive polymer, a photosensitive acid generator, and a dissolution inhibitor in which an acid-labile di-alkylmalonate group is combined as a functional group with a $C_1$ to $C_{20}$ hydrocarbon.

Preferably, the dissolution inhibitor is mixed at a ratio of from about 1 to 50% by weight based on the total weight of the photosensitive polymer.

Preferably, the photosensitive polymer is polymerized from: one or more monomers selected from the group comprising di-alkylmalonylmethylstyrene, alkoxystyrene derivative and (meth)acrylate derivative; and one monomer selected from the group comprising hydroxystyrene and hydroxystyrene derivative.

Preferably, the photosensitive polymer is a polymer combined with an acid-labile di-alkylmalonate group that binds to the backbone of the polymer.

According to another aspect of the second objective, there is provided a chemically amplified photoresist composition containing a photosensitive polymer mixture instead of the photosensitive polymer.

Preferably, the photosensitive polymer mixture comprises a copolymer A polymerized from alkoxystyrene or an alkoxystyrene derivative monomer and hydroxystyrene or a hydroxystyrene derivative monomer, and a copolymer B polymerized from a (meth)acrylate derivative monomer and hydroxystyrene or a hydroxystyrene derivative monomer.

Preferably, the photosensitive polymer mixture comprises a copolymer A polymerized from alkoxystyrene or an alkoxystyrene derivative monomer and hydroxystyrene or a hydroxystyrene derivative monomer, and a copolymer B polymerized from t-butoxycarbonyloxystyrene or a t-butoxycarbonyloxystyrene derivative monomer and hydroxystyrene or a hydroxystyrene derivative monomer Preferably, the mixing ratio of the copolymers A and B is from about 1:9 to 9:1.

In another embodiment, the photosensitive acid generator is mixed at a ratio of from about 1 to 15% by weight based on the total weight of the photosensitive polymer or the photosensitive polymer mixture. Also, the photosensitive acid generator may be selected from the group comprising triarylsulfonium salts, diaryliodonium salts and sulfonates.

Preferably, the photoresist composition further comprises an organic base of from about 0.01 to 2.0% by weight based on the total weight of the photosensitive polymer or the photosensitive polymer mixture. Also, the organic base may be selected from the group comprising triethylamine, triisobutylamine, triisooctylamine, diethanolamine and tri-ethanolamine.

Therefore, the chemically amplified photoresist composition containing the dissolution inhibitor is suitable for forming a pattern having an excellent profile due to its high contrast and high thermal decomposition temperature.

DESCRIPTION OF THE PREFERRED EMBODIMENTS

A dissolution inhibitor for making a chemically amplified photoresist, and a chemically amplified photoresist composition containing the dissolution inhibitor, according to the preferred embodiments of the present invention, will be hereinafter described in more detail. A photolithography process using the photoresist composition will also be described.

Dissolution Inhibitor of Chemically Amplified Photoresist

A dissolution inhibitor for a chemically amplified photoresist according to the present invention is a compound containing an acid-labile di-alkylmalonate group bound as a functional group to a $C_1$ to $C_{20}$ hydrocarbon.

The $C_1$ to $C_{20}$ hydrocarbon can be cyclohexane, dimethylenecyclohexane, xylene or methylnaphthalene, and the di-alkylmalonate group can be a di-ti-butylmalonate, di-tetrahydropyranyl malonate or di-trimethylsilylmalonate group.

The dissolution inhibitor of the present invention is represented by the following chemical formula (CF1).

(CF1)

In chemical formula (CF1), m is 1 or 2, R1 is $C_1$ to $C_{20}$ hydrocarbon, and R2 is t-butyl, tetrahydropyranyl or trimethylsilyl group.

In a preferred embodiment, R1 is a cyclohexyl, dimethylcyclohexyl, xylenyl or naphthalenylmethyl group.

The dissolution inhibitor of the present invention has very low solubility due to its bulky acid-labile functional group, the di-alkylmalonate group. However, after the photoresist has been exposed to ultraviolet light, the di-alkylmalonate group is hydrolyzed by acid to form a malonic acid group, markedly increasing solubility. The thermal stability of the di-alkylmalonate group makes the thermal decomposition temperature (Td) of the photoresist compositions of the present invention higher than the glass transition temperature (Tg is approximately 130° C.). Therefore, the photoresist film can be hardened by pre-baking before exposure, at temperatures higher above the glass transition temperature. The pre-bake prevents the formation of a defective pattern profile, such as a T-top, due to damage by contaminants.

Photosensitive Polymer for Photoresist

The chemically amplified photoresist of the present invention, composed of a photoresist composition and the dissolution inhibitor, is a polymer formed of one or more monomers including di-alkylmalonylmethylstyrene, alkoxystyrene derivative or acrylate derivative, and a hydroxystyrene monomer or hydroxystyrene derivative.

The photosensitive polymer may be a copolymer, terpolymer or tetrapolymer, In a preferred embodiment, the photosensitive polymer is expressed by the following chemical formula (CF2). In the chemical formula (CF2), R3 is t-butyl, tetrahydropyranyl or trimethylsilyl; R4, R5, R7, R9 and R10 are each independently hydrogen atom or methyl group; R6 is alkoxyl-1-ethyl, tetrahydropyranyl, t-butyl or t-butoxycarbonyl; R8 is t-butyl or tetrahydropyranyl group; and k/(k+l+m+n) is from about 0.0 to 0.5, l/(k+l+m+n) is from about 0.0 to 0.5, m/(k+l+m+n) is from about 0.0 to 0.5, and n/(k+l+m+n) is from about 0.5 to 0.99.

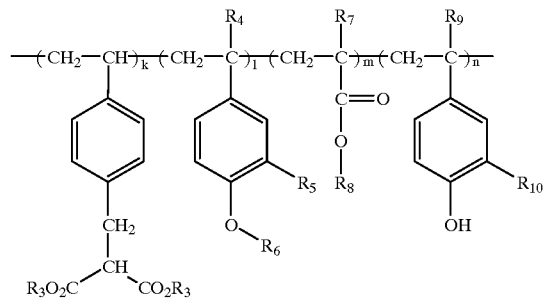
(CF2)

Preferably, a polymer in which an acid-labile di-alkylmalonate group, such as di-t-butyl malonate, di-tetrahydropyranyl malonate and di-trimethylsilyl malonate, is combined with the polymer's backbone, is used as the photosensitive polymer according to the present invention.

The polymer is bulky before exposure, however, after exposure, side chain groups are acid hydrolyzed R3, R6 or R8 combined with the backbone of the polymer malonic acid, hydroxy or carboxyl group by the acid generated during the exposure. Thus, solubility of the photoresist changes greatly during exposure. Also, because the side chain group is stable to heat, the photosensitive polymer has stable thermal characteristics at temperatures that are higher than the glass transition temperature.

Photosensitive Polymer Mixture for Photoresist

A photosensitive polymer mixture according to a first embodiment of the present invention, which comprises a photoresist composition together with the dissolution inhibitor, is a mixture of a copolymer A polymerized from a monomer of alkoxystyrene or alkoxystyrene derivative monomer, and a hydroxystyrene or hydroxystyrene derivative monomer; and a copolymer B polymerized from a monomer (meth)acrylate derivative monomer or a hydroxystyrene or hydroxystyrene derivative monomer. Preferably, the polymer mixture for a chemically amplified photoresist according to the first embodiment of the present invention is formed of the copolymers represented by the following chemical formulae (CF3) and (CF4).

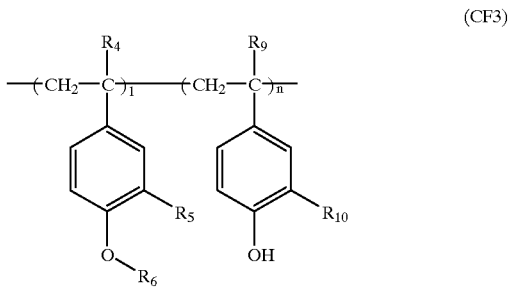
(CF3)

-continued

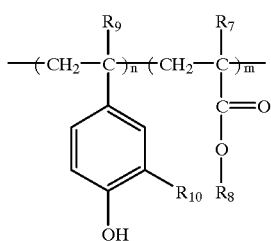
(CF4)

In the chemical formulae (CF3) and (CF4), R4, R5, R7, R9 and R10 are each independently a hydrogen atom or a methyl group; R6 is alkoxyl-1-ethyl, tetrahydropyranyl, t-butyl or t-butoxycarbonyl; R8 is a t-butyl or a tetrahydropyranyl group; l, m and n are integers, n/(n+l) is from about 0.5 to about 0.9, and n/(m+n) is from about 0.5 to about 0.9. In a preferred embodiment, R6 is a 1-ethoxyethyl group.

The mixing ratio of the copolymers represented by the chemical formulae (CF3) and (CF4) is from about 1:9 to about 9:1 and the weight average molecular weight of each polymer is from about 5,000 to 50,000.

A photosensitive polymer mixture according to a second embodiment of the present invention is a mixture of a copolymer A polymerized from a monomer of alkoxystyrene or an alkoxystyrene derivative, and a monomer of hydroxystyrene or hydroxystyrene derivative; and a copolymer B polymerized from a monomer of t-butoxycarbonyloxystyrene or a t-butoxycarbonyloxystyrene derivative, and a monomer of hydroxystyrene or a hydroxystyrene derivative monomer.

Preferably, the polymer mixture of the second embodiment is formed of the polymers represented by the following chemical formulae (CF3) and (CF5).

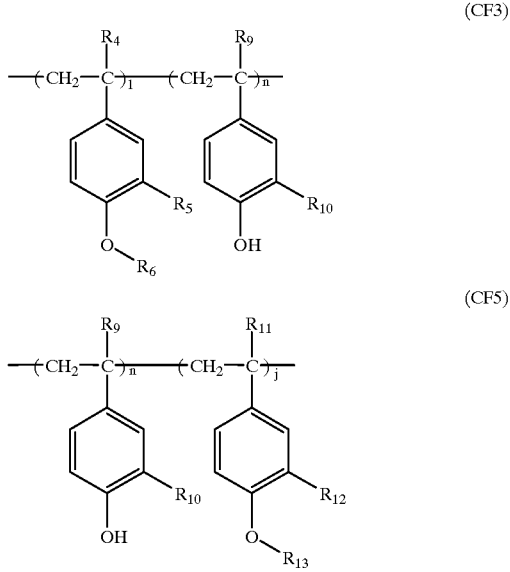

In chemical formulae (CF3) and (CF5), R4, R5, R9, R10, R11 and R12 are each independently a hydrogen atom or a methyl group; R6 is alkoxyl-1ethyl, tetrahydropyranyl, t-butyl or t-butoxycarbonyl; R13 is a t-butoxycarbonyl group; and j, l and n are integers, n/(l+n) is from about 0.5 to about 0.9 and n/(j+n) is from about 0.5 to about 0.9.

The mixing ratio of the polymers represented by the chemical formulae (CF3) and (CF5) is preferably from about 1:9 to about 9:1 and the weight average molecular weight of each polymer is about 5,000 to 50,000.

Chemically Amplified Photoresist Composition

A chemically amplified photoresist composition according to the present invention includes a photosensitive polymer or polymer mixture, a dissolution inhibitor and a photosensitive acid generator.

The dissolution inhibitor is preferably mixed at a ratio of from about 1 to 50% by weight based on the total weight of the photosensitive polymer or polymer mixture.

The photosensitive acid generator is preferably mixed at a ratio of about 1 to about 15% by weight based on the total weight of the photosensitive polymer or polymer mixture, and the photosensitive acid generator. The photosensitive acid generator may be a triarylsulfonium salt, a diaryliodonium salt, or a sulfonate. Photosensitive acid generators which may be used in the present invention include triphenylsulfonium triflate, triphenylsulfonium antimonate, diphenyliodonium triflate, diphenylidonium antimonate, methoxydiphenyliodonium triflate, di-t-butyldiphenyliodonium triflate, 2,6,-dinitrobenzylsulfonate, pyrogallol tris(alkylsulfonate) and N-hydroxysuccinimide triflate.

In another preferred embodiment, the photoresist composition according to the present invention further contains an organic base in an amount of from about 0.01 to 2.0 weight percent based on the weight of the polymer. Some examples of a suitable organic base for use in the present invention are triethylamine, triisobutylamine, diethanolamine and triethanolamine. The organic base prevents a decrease in a critical size of the pattern after exposure, caused by acid diffusing from an exposed portion of the photoresist to a unexposed portion. It also ensures that the overall acid concentration remains uniform, even if neutralization should occur at the surface caused by external contaminants.

As described above, the photoresist composition of the present invention includes a dissolution inhibitor with which an acid-labile di-alkylmalonate group, e.g., di-t-butyl malonate, di-tetrahydropyranyl malonate or di-trimethylsilyl malonate, is combined as a functional group. The bulky di-alkylmalonate group is hydrolyzed into malonic acid by the acid generated by the photosensitive acid generator through exposure to light. The hydrolysis to malonic acid results in a significant increase in solubility of the photoresist composition before and after exposure. This difference in solubility is observed as a difference in contrast. An important advantage of the photoresist composition according to the present invention, is that the di-alkylmalonate group and the photosensitive acid generator, which are themselves thermally stable, confer thermal stability on the photoresist composition at a temperature referred to as the thermal decomposition temperature, which is higher than its glass transition temperature (approximately 130° C.). This means that a wafer coated with the photoresist composition of the present invention can be pre-baked at a temperature that is higher than its glass transition temperature, but lower than its decomposition temperature. The pre-bake prevents contaminants from being absorbed into the photoresist where they interfere with the function of the photosensitive acid generator.

The photosensitive polymer (or photosensitive polymer mixture) of the present invention is also very bulky before the photoresist is exposed. However, the acid generated by exposure to light causes a side chain group bound to the backbone of the polymer to leave, thus forming a malonate, hydroxy or carboxyl group. This hydrolysis markedly increases the solubility of the photoresist. The thermally stable side chain group confers thermal stability on the photosensitive polymer so that the decomposition temperature (Td) is higher than the glass transition temperature (Tg).

Preparation Method of a Dissolution Inhibitor for Chemically Amplified Photoresist Preparation Method of a Hydrocarbon Compound Having di-alkylamlonate Group as a Functional Group As shown in reaction formula (RF1), after dissolving di-alkylmalonate (II) in a tetrahydrofuran (THF) solution in which sodium hydride has been dissolved, a halogen compound (I) is added to form a di-alkylmalonylhydrocarbon compound (III) through a substitution reaction.

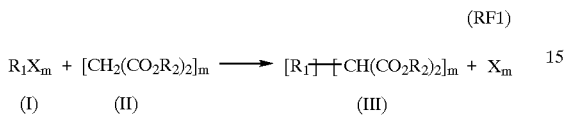

(RF1)

In reaction formula (RF1), m is 1 or 2, R1 is $C_1$ to $C_{20}$ hydrocarbon, R2 is a t-butyl, tetrahydropyranyl or trimethylsilyl group, and X is halogen.

Preferably, the $C_1$ to $C_{20}$ hydrocarbon is cyclohexane, dimethylenecyclohexane, xylene or methylnaphthalen.

Preparation Method of a Photosensitive Polymer or a Photosensitive Polymer Compound 1. Preparation Method of a Polymer Having di-alkylmalonate Functional Group 1-1. Preparation of a Monomer: Preparation of di-alkylmalonylmethylstyrene (VI)

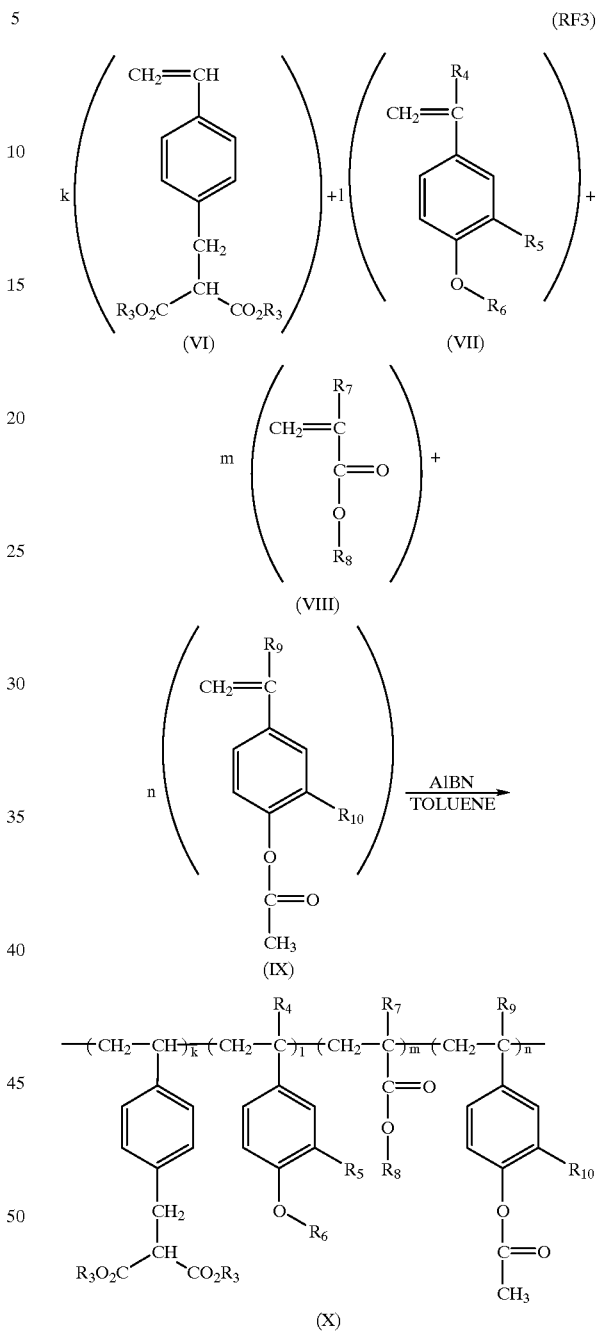

As shown in reaction formula (RF2), after dissolving di-alkylmalonate (V) in an organic solvent such as tetrahydrofuran THF which sodium hydride has been dissolved, chloromethylstyrene (IV) is added to the solution. Di-alkylmalonylmethylstyrene (VI) then formed through a substitution reaction.

In the reaction formula (RF2), R3 is a t-butyl, tetrahydropyranyl or trimethylsilyl group.

1-2. Preparation of Polymer (XI)

Here, a polymer (XI) is polymerized from one or more monomers selected from the group comprising di-alkylmalonylmethylstyrene (VI), alkoxystyrene derivative (VII) and (meth)acrylate derivative (VIII), and hydroxystyrene or hydroxystyrene derivative monomer.

1-2-1. Polymerization

A polymer (X) is formed through polymerization as shown in the following reaction formula (RF3).

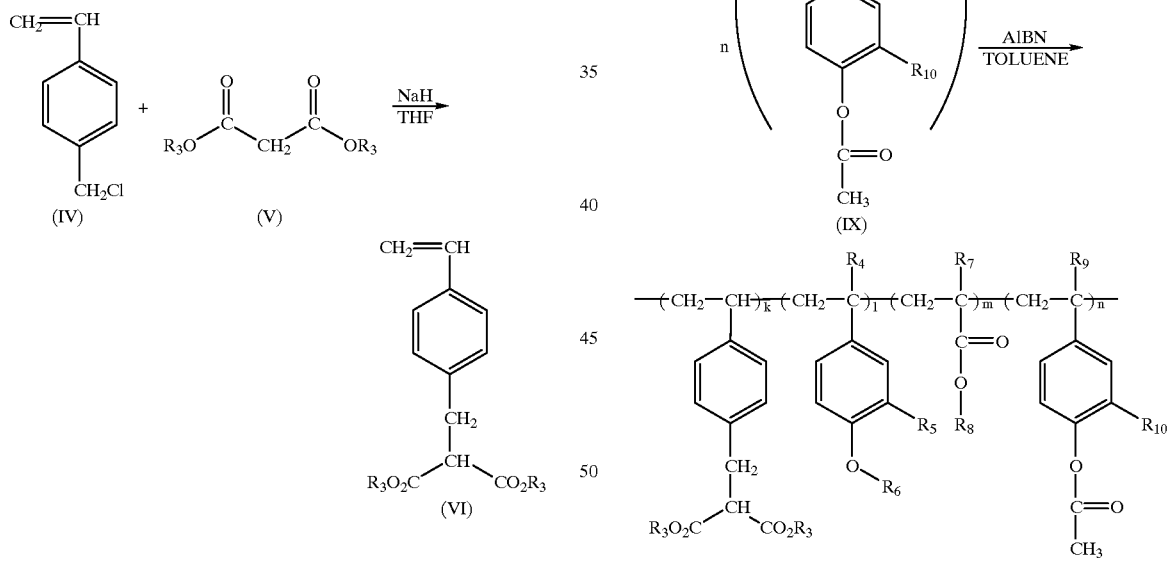

In the reaction formula (RF3), R3 is a t-butyl, tetrahydropyranyl or trimethylsilyl group; R4, R5, R7, R9 and R10 are each independently a hydrogen atom or a methyl group; R6 is alkoxyl-1-ethyl, tetrahydropyranyl, t-butyl or t-butoxycarbonyl; R8 is a t-butyl or tetrahydropyranyl group; and k/(k+l+m+n) is from about 0.0 to 0.5, l/(k+l+m+n) is from about 0.0 to 0.5, m/(k+l+m+n) is from about 0.0 to 0.5, and n/(k+l+m+n) is from about 0.5 to 0.99.

One or more monomers selected from the group including di-alkylmalonylmethylstyrene (VI), alkoxystyrene derivative (VII) and (meth)acrylate derivative (VIII), and an acetoxystyrene or acetoxystyrene derivative monomer (IX)

in an organic solvent, e.g., toluene. Then a polymerization initiator, e.g., azobisisobutyronitrile (AIBN), is added to obtain a polymer (X).

1-2-2. Deacetylation of Polymer (X)

As shown in the following reaction formula (RF4), the polymer (X) is deacetylated using an organic base, resulting in a polymer (XI) having a weight average molecular weight of from about 5,000 to about 100,000, represented by the chemical formula (CF2). Here, ammonium hydroxide or hydrazine is used as the organic base.

wherein n is the number of acetoxystyrene or acetoxystyrene derivative monomers, and j is the number of the t-butoxycarbonyloxystyrene or t-butoxycarbonyloxystyrene derivative monomers. Then, the deacetylation step is performed, resulting in the copolymer represented by the chemical formula (CF5) and having a weight average molecular weight of from about 5,000 to 50,000.

Preparation Method of a Chemically Amplified Photoresist Composition, and a Photolithography Method Using the Chemically Amplified Photoresist Composition

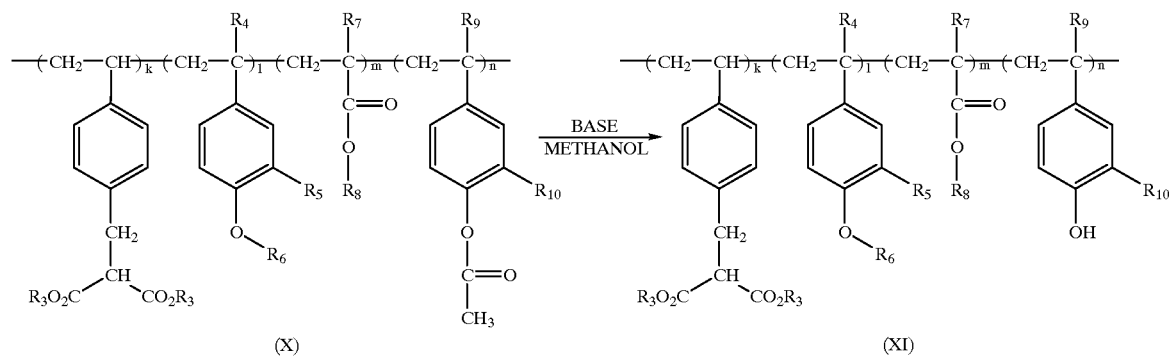

(RF4)

2. Preparation Method of a Photosensitive Polymer Mixture
2-1. Preparation of Copolymer Expressed by the Chemical Formula (CF3)

The copolymer represented by the chemical formula (CF3) is formed of a monomer of alkoxystyrene or an alkoxystyrene derivative, and a monomer of hydroxystyrene or hydroxystyrene derivative.

A copolymer is prepared such that k and m are set to equal 0 and n/(n+l) is set to be from about 0.5 to 0.9 in reaction formula (RF3). Next, the deacetylation step shown in reaction formula (RF4) is performed, resulting in the copolymer represented by the chemical formula (CF3) and having a weight average molecular weight of from about 5,000 to 50,000.

2-2. Preparation of a Copolymer Represented by the Chemical Formula (CF4)

The copolymer represented by the chemical formula (CF4) is formed of a monomer of hydroxystyrene or hydroxystyrene derivative and a monomer of (meth)acrylate derivative.

A copolymer is prepared such that k and l are set to equal 0 and n/(m+n) is set to be from about 0.5 to 0.9 in reaction formula (RF3). Next, the deacetylation step of reaction formula (RF4) is performed, resulting in the copolymer represented by chemical formula (CF4) and having a weight average molecular weight of from about 5,000 to 50,000.

2-3 Preparation of a Copolymer Represented by the Chemical Formula (CF5)

The copolymer represented by the chemical formula (CF5) is formed of a monomer of hydroxystyrene or hydroxystyrene derivative, and a monomer of t-butoxycarbonyloxystyrene or t-butoxycarbonyloxystyrene derivative.

The copolymer is formed such that the acetoxystyrene or acetoxystyrene derivative monomer and the t-butoxycarbonyloxystyrene or t-butoxycarbonyloxystyrene derivative monomer are mixed at a ratio of from about 0.5 to 0.9. Here, the mixing ratio is represented by n/(j+n), In the preparation method of a chemically amplified photoresist composition according to the present invention, the photosensitive polymer represented by the chemical formula (CF2), the mixture of the photosensitive polymers represented by the chemical formulae (CF3) and (CF4), or the mixture of the photosensitive polymers represented by the chemical formulae (CF3) and (CF5), are dissolved together with the dissolution inhibitor represented by the chemical formula (CF1) and the photosensitive acid generator, in an appropriate solution, to form a photoresist composition.

The dissolution inhibitor represented by the chemical formula (CF1) is mixed at a ratio of from about 1 to 50% by weight based on the total weight of the polymer or polymer mixture, and the photosensitive acid generator is mixed at a ratio of from about 1 to 15% by weight based on the total weight of the polymer or polymer mixture. Preferably, the photosensitive acid generator is a triarylsulfonium salt, a diaryliodonium salt or a sulfonate, which are thermally stable compounds.

Preferably, an organic base of from about 0.01 to 2.0% by weight based on the weight of the polymer or polymer mixture is further dissolved in the mixture to form the photoresist composition. Preferably, the organic base is triethylamine, triisobutylamine, triisooctylamine, diethanolamine, triethanolamine, or N-methyl pyrrolidone.

The chemically amplified photoresist composition formed by the above method may be applied to a general photolithography process. The chemically amplified photoresist composition is particularly suitable for forming a fine pattern having a design rule of about 0.25 $\mu$m or less, using deep ultraviolet (UV) rays of about 248 nm as a light source for exposure.

First, the above-described photoresist composition is deposited on a substrate having a target to be patterned, to form a photoresist film having a predetermined thickness. The photoresist film is pre-baked before exposure. Because the photoresist composition contains a di-alkylmalonate group and a photosensitive acid generator which are both thermally stable, the composition has a thermal decomposition temperature Td (approximately 170° C. or more) that is higher than the glass transition temperature Tg (approximately 130° C.). This means that before exposing the photoresist film, the photoresist film can be pre-baked at a temperature higher than the glass transition temperature, to harden the photoresist film. Thus, inhibition of the function of the photosensitive acid within the exposed portion caused by airborne contaminants being absorbed in the photoresist film, can be effectively prevented. Using the photoresist compositions of the present invention prevents formation of a defective pattern such as a T-top profile, and permits the formation of a fine pattern having an intended profile.

After pre-baking, the photoresist film is exposed to deep ultraviolet rays, using a mask that has a predetermined pattern. Acid, generated by the photosensitive acid generator in the photoresist film by exposure to UV rays, hydrolyzes the di-alkylmalonate of the dissolution inhibitor to malonic acid by catalytic reaction according to reaction formula (RF5). A post-exposure thermal treatment is performed on the photoresist film for a short time before development in order to facilitate completion of the acid hydrolysis by a catalytic reaction of acid within the exposed portion of the photoresist. This post-exposure thermal treatment is to completely convert di-alkylmalonate within the exposed portion into malonic acid. As is shown in reaction formula (RF6), the di-alkylmalonate, alkoxyl or ester group of the photosensitive polymer is acid hydrolyzed to form, a hydroxy or carboxyl group. The hydrolysis to malonic acid results in a significant difference in polarity between the exposed portion of the photoresist film and the polarity of the non-exposed portion. This difference in solubility is observed as a difference in contrast which is high.

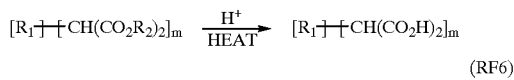
(RF5)

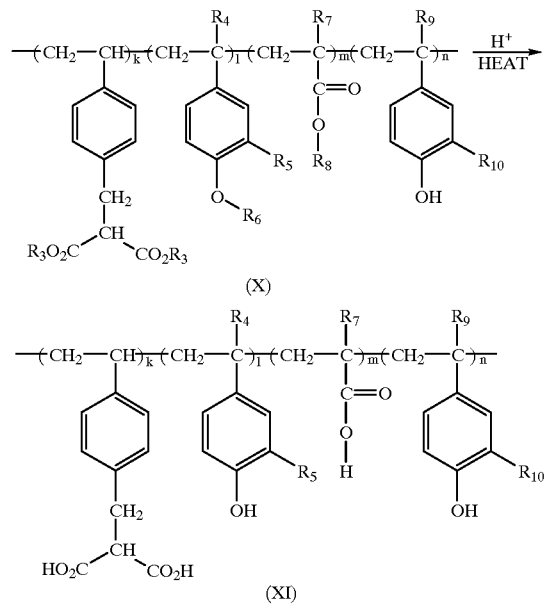

Next, a developing process is performed using an appropriate developer liquid which is selected depending on whether the photoresist film is used for a positive or negative purpose. Then, general processes known to those skilled in the art are performed to complete the photoresist pattern.

When forming a photoresist pattern using the photoresist composition of the present invention, a high resolution pattern having a good profile can be formed.

The present invention will be described through the following nonlimiting examples.

EXAMPLE 1

Preparation of a Dissolution Inhibitor 1-1. Preparation of 1,4-bis(di-t-butylmalonyl)cyclohexane 2.9 g of sodium hydride (0.12 mol) was dissolved in 250 ml of tetrahydrofuran (THF). 25 g of di-t-butylmalonate (0.11 mol) was slowly dropped into the solution and reacted for about 1 hour. Then, 2.1 g of 1,4-dibromocyclohexane (0.05 mol) was slowly dropped into the mixture at 0° C., and reacted for 12 hours at 45° C. After the reaction was complete, the solvent THF was evaporated from the reaction product. Then, the resultant product was dissolved in water, neutralized with hydrochloric acid, and extracted using diethyl ether.

After drying the obtained crude product using magnesium sulfate, the reaction product was separated using column chromatography (yield 55%).

1-2. Preparation of a 1.4-bis(di-t-butylmalonyl)-p-xylene

The same processes as in the above section (1-1) were performed, except that 12.1 g of dibromo-p-xylene (0.05 mol) was used instead of 1,4-dibromocyclohexane.

After drying the obtained crude product using magnesium sulfate, the reaction product was separated using column chromatography (yield 55%).

EXAMPLE 2

Preparation of a di-t-butylmalonylmethylstyrene Monomer 2.9 g of sodium hydride (0.12 mol) was dissolved in 250 ml of THF. 25 g of di-t-butylmalonate (0.11 mol) was slowly dropped into the solution and reacted for about 1 hour. Then, 0.1 mol of chloromethylstyrene was slowly dropped into the mixture at 0° C., and reacted for 12 hours at room temperature. After the substitution reaction was completed, the reaction product was dissolved in water, neutralized with hydrochloric acid, and then extracted using diethyl ether.

After drying the obtained crude product using magnesium sulfate, the reaction product was separated using column chromatography (yield 65%).

Nuclear magnetic resonance (NMR) and Fourier transform infrared (FT-IR) spectroscopy analyses performed on the reaction product showed that the product was di-t-butylmalonylmethylstyrene.

$^1$H -NMR(CDCl$_3$)(ppm):
1.4(s,18H), 3.1(d,2H), 3.5(t,1H),5.2(dd,1H), 5.7(dd, 1H), 6.6(dd,1 H), 7.2(m,4H)

FT-IR(NaCl)(cm$^{-1}$):2978(C-H,t-butyl),1727(C=O), 1369, 1140, 847

EXAMPLE 3

Preparation of a Photosensitive Copolymer 3-1. Preparation of a Copolymer Polymerized di-t-butylmalonylmethylstyrene and Hydroxystyrene Monomers 3 g of di-t-butylmalonylmethylstyrene (9 mmol) and 7.5 g of acetoxystyrene (45 mmol) were dissolved in 50 ml of toluene. Then, 0.44 g of azobisisobutyronitrile (AIBN) was added, and purged using nitrogen gas for 1 hour, and polymerization was performed for about 24 hours at 70° C.

After the polymerization, the product was precipitated in n-hexane (about 10 times), and the precipitate was dried in a vacuum oven maintained at a temperature of 50° C. for about 24 hours to separate the reaction product (yield 70%).

The obtained reaction product was a copolymer containing di-t-butylmalonylmethylstyrene and hydroxystyrene monomers, having a weight average molecular weight of 12,157 and a polydispersity of 1.6.

10 g of the obtained product was added to 10 ml of ammonium hydroxide (28%), and refluxed for 4 hours to accomplish the deacetylation step. Then, the reaction product was slowly precipitated in water.

The precipitate was dissolved in THF, reprecipitated in n-hexane, and then dried at a vacuum oven maintained at a temperature of 50° C. to separate the reaction product (yield 90%).

The obtained reaction product was a copolymer containing di-t-butylmalonylmethylstyrene and hydroxystyrene monomers, having a weight average molecular weight of 11,438 and a polydispersity of 1.67.

3-2. Preparation of a Copolymer Using Poly(hydroxystyrene) and Ethylvinylether 12 g of poly(hydroxystyrene) was dissolved in 60 ml of THF and 3.6 g of ethylvinylether was added. A small amount of p-toluenesulfonic acid (p-TSA) to act as a catalyst was added and reacted at 40° C. for 12 hours. After the reaction was complete, the reaction product was slowly dropped into an excess amount of water and neutralized with potassium carbonate.

The precipitant was dissolved in THF, reprecipitated in n-hexane, and then dried in a vacuum oven maintained at a temperature of 50° C. to separate the reaction product (yield 85%).

The obtained reaction product was a copolymer. A weight average molecular weight was 12,285, a polydispersity was 1.67 and transmittance against ultraviolet rays was 73%/$\mu$m.

3-3. Preparation of a Copolymer Using Poly(hydroxystyrene) and 3,4-dihydro-2-pyran A copolymer containing tetrahydropyranoxystyrene and hydroxystyrene monomers was prepared by the same processes as in the above section (3-2) except that 4.2 g of 3,4-dihydro-2-pyran was used instead of ethylvinylether (yield 80%).

The obtained copolymer had a weight average molecular weight of 13,587 and a polydispersity of 1.74.

3-4. Preparation of Copolymer Using Poly(hydroxystyrene) and t-butoxycarbonate

A copolymer containing t-butoxystyrene and hydroxystyrene monomers was prepared by the same processes as in the above section (3-2) except that di-t-butoxycarbonate was used instead of ethylvinylether (yield 85%).

The obtained copolymer had a weight average molecular weight of 13,889 and a polydispersity of 1.8.

3-5. Preparation of Copolymer Polymerized Hydroxystyrene and t-butylacrylate Monomers 20 g of acetoxystyrene (120 mmol) and 7.8 g of t-butylacrylate (60 mmol) were dissolved in 140 ml of toluene. The reaction product was separated by the same processes as in the above section (3-1), except that 1.48 g of AIBN was added.

The obtained reaction product was a copolymer containing acetoxystyrene and t-butylacrylate monomers, and having a weight average molecular weight of 12,017 and a polydispersity of 1.83.

The obtained reaction product was deacetylated by the same method as in the above section (3-2), resulting in a copolymer containing t-butylacrylate and hydroxystyrene monomers, and having a weight average molecular weight of 11,438 and a polydispersity of 1.82.

EXAMPLE 4

Preparation of Photosensitive Terpolymer 4-1. Preparation of Terpolymer Containing Hydroxystyrene, t-butylacrylate and di-t-butylmalonylmethylstyrene Monomers 11.11 g of acetoxystyrene (70 mmol), 2.6 g of t-butylacrylate (20 mmol) and 3.4 g of di-t-butylmalonylmethylstyrene (10 mmol) were dissolved in 75 ml of toluene. Then, 0.82 g of AIBN was added, and purged using nitrogen gas for 1 hour. Polymerization was performed for about 24 hours at 70° C.

After the polymerization, the reaction product was precipitated in n-hexane (about 10 times), and the precipitate was dried in a vacuum oven maintained at a temperature of 50° C. for about 24 hours to separate the reaction product (yield 70%).

The obtained reaction product had a weight average molecular weight of 12,557 and a polydispersity of 1.98.

10 g of the obtained reaction product was added to a mixture of 10 ml of ammonium hydroxide (28%) and 50 ml of methanol, and refluxed for 4 hours to accomplish the deacetylation step. Then, the reaction product was slowly precipitated in water.

The precipitant was dissolved in THF, reprecipitated in n-hexane, and then dried in a vacuum oven maintained at a temperature of 50° C. to separate the reaction product (yield 90%).

The obtained reaction product was a terpolymer containing hydroxystyrene, butylacrylate and di-t-butylmalonylmethylstyrene monomers at a ratio of 70:25:5, having a weight average molecular weight of 11,438 and a polydispersity of 1.97.

4-2. Preparation of a Terpolymer Containing Hydroxystyrene, t-butoxystyrene and di-t-butylmalonylmethylstyrene Monomers 10.5 g of acetoxystyrene (63 mmol), 3.2 g of t-butoxystyrene (18 mmol) and 3 g of di-t-butylmalonylmethylstyrene (9 mmol) were dissolved in 80 ml of toluene. A terpolymer was prepared by the same processes and under the same conditions as in the above section (4-1) except that 0.74 g of AIBN was added (yield 80%).

The obtained reaction product was a terpolymer containing hydroxystyrene, t-butoxystyrene and di-t-butylmalonylmethylstyrene at a ratio of 70:20:10. A weight average molecular weight of the product was 12,639, the polydispersity was 1.85, and transmittance against ultraviolet rays was 73%/$\mu$m.

4-3. Preparation of a Terpolymer Containing Hydroxystyrene, t-butylacrylate and t-butoxystyrene Monomers 9.7 g of acetoxystyrene (60 mmol), 4.3 g of t-butylacrylate (30 mmol) and 1.8 g of butoxystyrene (10 mmol) were dissolved in 80 ml of toluene. A terpolymer was prepared by the same processes and under the same conditions as in the above section (4-1) except that 0.67 g of AIBN was added (yield 85%).

The obtained reaction product was a terpolymer having a weight average molecular weight of 11,537 and a polydispersity of 1.93.

EXAMPLE 5

Preparation of a Tetrapolymer Containing Hydroxystyrene, t-butylacrylate, t-butoxystyrene and di-t-butylmalonylmethylstyrene Monomers 9.7 g of acetoxystyrene (60 mmol), 2.8 g of t-butylacrylate (20 mmol), 1.8 g of t-butoxystyrene (10 mmol) and 3.4 g of di-t-butylmalonylmethylstyrene (10 mmol) were dissolved in 90 ml of toluene. A tetrapolymer was prepared by the same processes and under the same conditions as in the above section (4-1) except that 0.67 g of AIBN was added (yield 80%).

The obtained reaction product was a tetrapolymer having a weight average molecular weight of 12,430 and a polydispersity of 1.87.

EXAMPLE 6

Preparation of Photoresist Composition and Photolithography Using the Same 6-1. Preparation of a Photoresist Composition Containing 1,4-bis(di-t-butylmalonyl)cyclohexane as a Dissolution Inhibitor, a Photosensitive Copolymer and a Photosensitive Acid Generator, and a Photolithography Process 1.0 g of the photosensitive copolymer prepared as in (3-1) and containing hydroxystyrene and di-t-butylmalonylmethylstyrene monomers, 0.03 g of triphenylsulfonium triflate (TPSOTf) as a photosensitive acid generator, and 0.2 g of 1,4-bis(di-t-butylmalonyl) cyclohexane prepared as in (1-1), were completely dissolved in 6 g of propylene glycol monomethyl ether acetate (PGMEA), then filtered through a filter having pores of 0.2, μm, resulting in a photoresist composition.

The obtained photoresist composition was spin-coated onto a wafer having a material layer thereon to be patterned, to a thickness of approximately 0.5, μm. The wafer coated with the photoresist composition was soft-baked at approximately 130° C. for about 90 seconds, exposed using a mask defining a patten with a 0.40 μm line and space arrays and a stepper using a KrF eximer laser having a numerical aperture (NA) of 0.45. The photoresist was then post-baked at approximately 140° C. for about 90 seconds. Then, the resultant photoresist layer was developed using 2.38% by weight of tetramethylammonium hydroxide for 60 seconds to form a photoresist pattern. The material layer under the photoresist pattern was then etched.

Using this photoresist composition and photolithography method, a photoresist pattern having an excellent profile with 0.40, μm line and space arrays was formed with an exposure energy of 18 mJ/cm².

6-2. Preparation of a Photoresist Composition Containing bis(di-t- butylmalonyl)-p-xylene as a Dissolution Inhibitor, a Photosensitive Copolymer and a Photosensitive Acid Generator, and a Photolithography Process A photoresist composition was prepared and photolithography was performed, by the same methods as in the above section (6-1) except that 0.2 g of bis(di-t-butylmalonyl)-p-xylene was used as the dissolution inhibitor, instead of 1,4-bis(di-t-butylmalonyl)cyclohexane.

Using this photoresist composition and photolithography method, a photoresist pattern having an excellent profile with 0.40 μm line and space arrays was formed with an exposure energy of 21 mJ/cm².

6-3. Preparation of a Photoresist Composition Containing bis(di-t-butylmalonyl)-p-xylene as a Dissolution Inhibitor, a Photosensitive Copolymer, a Photosensitive Acid Generator and an Organic Base, and a Photolithography Process A photoresist composition was prepared and photolithography was performed, by the same method as in the above section (6-2) except that 1 mg of triethylamine was further added as an organic base.

Using this photoresist composition and photolithography method, a photoresist pattern having an excellent profile with 0.40 μm line and space arrays was formed with an exposure energy of 33 mJ/cm².

6-4. Preparation of a Photoresist Composition Containing bis(di-t-butylmalonyl)-p-xylene as a Dissolution Inhibitor, a Photosensitive Terpolymer and a Photosensitive Acid Generator, and a Photolithography Process A photoresist composition was prepared and photolithography was performed, by the same method as in the above section (6-2), except that 1.0 g of terpolymer containing hydroxystyrene, t-butylacrylate and di-t-butylmalonylmethylstyrene monomers, prepared as per the above section (4-1), was used instead of the photosensitive copolymer.

Using this photoresist composition and photolithography method, a photoresist pattern having an excellent profile with 0.40 μm line and space arrays was formed with an exposure energy of 24 mJ/cm².

6.5 Preparation of a Photoresist Composition Containing bis(di-t-butylmalonyl)-p-xylene as a Dissolution Inhibitor, a Photosensitive Terpolymer, a Photosensitive Acid Generator and an Organic Base, and a Photolithography Process A photoresist composition was prepared and photolithography was performed by the same methods as in the above section (6-4) except that 1 mg of triethylamine was further added as an organic base.

Using this photoresist composition and photolithography method, a photoresist pattern having an excellent profile with 0.40 μm line and space arrays was formed with an exposure energy of 36 mJ/cm².

The dissolution inhibitor according to the present invention has an acid-labile di-alkylmalonate group as a functional group, to greatly increase the difference in solubility of the chemically amplified photoresist composition after exposure. This solubility difference is responsible for creating a high contrast. The di-alkylmalonate group, e.g., the di-t-butylmalonate, di-tetrahydropyranylmalonate or di-trimethylsilyl malonate group, is very bulky, and its solubility is very low before exposure. However, the di-alkylmalonate group is hydrolyzed to malonic acid by the acid generated by the photosensitive acid generator during exposure, thereby maximizing solubility of the exposed chemically amplified photoresist composition. Thus, the solubility difference before and after exposure, that is, contrast, is significantly higher than what is obtained using a conventional photoresist composition having a t-butoxycarbonyl (t-BOC) group.

The photosensitive polymer, like the dissolution inhibitor, has a bulky di-alkylmalonate group, alkoxyl group or ester group. Upon being exposed, these bulky groups are acid hydrolyzed to a malonic acid, hydroxy or carboxyl group which has a higher polarity. Thus, polarity of the photoresist film in the exposed portion and the non-exposed portion becomes very different, increasing contrast.

The dissolution inhibitor, photosensitive polymer and photosensitive acid generator according to the present invention have excellent thermal characteristics, so the photoresist composition containing those has a thermal decomposition temperature higher than a glass transition temperature (approximately 130° C.). Before exposing the photoresist film, the photoresist film can be pre-baked at a temperature higher than the glass transition temperature, to harden the photoresist film. Thus, inhibition of the function of the acid within the exposed portion, by airborne contaminants adsorbed by the photoresist film, can be effectively prevented. As a result, pattern defects such as a T-top profile are prevented, and a fine pattern having an intended profile can be formed using the dissolution inhibitors, and the chemically amplified photoresists.

Although preferred embodiments of the present invention have been described in detail hereinabove, many variations and/or modifications of the basic inventive concepts herein taught will appear to those skilled in the art. All such variations and/or modifications fall within the spirit and scope of the present invention as defined in the appended claims.

What is claimed is:

1. A dissolution inhibitor of a chemically amplified photoresist, comprising an acid-labile di-alkylmalonate group bound to a $C_1$ to $C_{20}$ hydrocarbons wherein the $C_1$ to $C_{20}$ hydrocarbon is selected from the group consisting of cyclohexane, dimethylenecyclohexane, xylene and methyinaphthalene, and wherein the di-alkylmalonate group is selected from the group consisting of di-t-butylmalonate, di-tetrahydropyranyl malonate and di-trimethylsilylmalonate.

2. The dissolution inhibitor of claim 1, wherein the dissolution inhibitor of the photoresist is represented by the following chemical formula (CF1):

(CF1)

wherein m is 1 or 2; R1 is a $C_1$ to $C_{20}$ hydrocarbon; and R2 is selected from the group comprising a t-butyl, tetrahydropyranyl group and a trimethylsilyl group, and wherein R1 is selected from the group comprising cyclohexyl, dimethylcyclohexyl. xylenyl and naphthalenylmethyl groups.

3. A chemically amplified photoresist composition comprising:

a photosensitive polymer, a photosensitive acid generator, and a dissolution inhibitor in which an acid-labile di-alkylmalonate group is bound to a $C_1$ to $C_{20}$ hydrocarbons wherein the $C_1$ to $C_{20}$ hydrocarbon is selected from the group consisting of cyclohexane, dimethylenecyclohexane, xylene and methylnaphthalene, and wherein the di-alkylmalonate group is selected from the group consisting of di-t-butylmalonate, di-tetrahydropyranyl malonate and di-trimethylsilylmalonate.

4. The chemically amplified photoresist composition of claim 3, wherein the dissolution inhibitor is represented by the following chemical formula (CF1):

(CF1)

wherein m is 1 or 2; R1 is a $C_1$ to $C_{20}$ hydrocarbon; and R2 is selected from the group comprising a t-butyl, tetrahydropyranyl group and a trimethylsilyl group, and wherein the $C_1$ to $C_{20}$ hydrocarbon is selected from the group comprising cyclohexane, dimethylenecyclohexane, xylene and methylnaphthalene.

5. The chemically amplified photoresist composition of claim 3, wherein the dissolution inhibitor is mixed at a ratio of from about 1% to about 50% by weight based on the total weight of the photosensitive polymer.

6. The chemically amplified photoresist composition of claim 3, wherein the photosensitive polymer is polymerized from:

one or more monomers selected from the group comprising di-alkylmalonylmethylstyrene, alkoxystyrene derivative and a (meth)acrylate derivative, and one monomer selected from the group comprising hydroxystyrene and a hydroxystyrene derivative.

7. The chemically amplified photoresist composition of claim 6, further comprising an acid-labile di-alkylmalonate group bound to a backbone of the photosensitive polymer, and the di-alkylmalonate group is selected from the group comprising a di-t-butylmalonate group, a di-tetrahydropyranylmalonate group and a di-trimethylsilyl group.

8. The chemically amplified photoresist composition of claim 7, wherein the photosensitive polymer is represented by the following chemical formula (CF2):

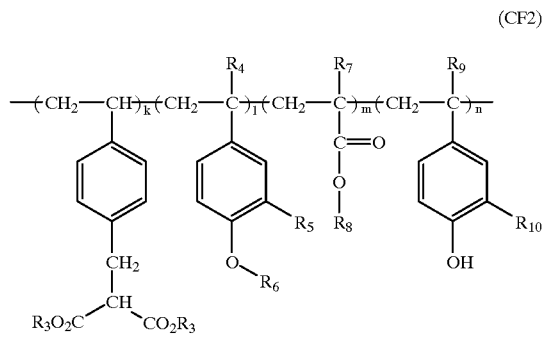

(CF2)

wherein R3 is selected from the group comprising t-butyl, tetrahydropyranyl and trimethylsilyl;

R4, R5, R7, R9 and R10 are each independently one selected from the group comprising of a hydrogen atom and a methyl group;

R6 is selected from the group comprising alkoxyl-1-ethyl, tetrahydropyranyl, t-butyl and t-butoxycarbonyl;

R8 is selected from the group comprising a t-butyl group and atetrahydropyranyl group;

k/(k+l+m+n) is from about 0.0 to 0.5, l/(k+l+m+n) is from about 0.0 to 0.5, m/(k+l+m+n) is from about 0.0 to 0.5, n/(k+l+m+n) is from about 0.5 to 0.99; and the weight average molecular weight of the polymer is from about 5,000 to 100,000.

9. The chemically amplified photoresist composition of claim 3, wherein the photosensitive acid generator is mixed at a ratio of from about 1 to 15% by weight based on the total weight of the photosensitive polymer.

10. The chemically amplified photoresist composition of claim 3, wherein the photosensitive acid generator is selected from the group comprising triarylsulfonium salts, diaryliodonium salts and sulfonates.

11. The chemically amplified photoresist composition of claim 3, further comprising an organic base of from about 0.01 to 2.0% by weight based on the total weight of the photosensitive polymer.

12. The chemically amplified photoresist composition of claim 11, wherein the organic base is selected from the group comprising triethylamine, triisobutylamine, triisooctylamine, diethanolamine, triethanolamine, and N-methyl pyrrolidone.

13. The chemically amplified photoresist composition of claim 12, wherein the dissolution inhibitor is mixed at a ratio of from about 1 to 50% by weight based on the total weight of the photosensitive polymer.

14. A chemically amplified photoresist composition comprising:

a photosensitive polymer mixture;

a photosensitive acid generator; and a dissolution inhibitor in which an acid-labile di-alkylmalonate group is bound to a $C_1$ to $C_{20}$ hydrocarbon, wherein the $C_1$ to $C_{20}$ hydrocarbon is selected from the group consisting of cyclohexane, dimethylenecyclohexane, xylene and methylnaphthalene, and wherein the di-alkylmalonate group is selected from the group consisting of di-t-butylmalonate, di-tetrahydropyranyl malonate and di-trimethylsilylmalonate.

15. The chemically amplified photoresist composition of claim 14, wherein the dissolution inhibitor is represented by the following chemical formula (CF1):

   (CF1)

wherein m is 1 or 2; R1 is $C_1$ to $C_{20}$ hydrocarbon; and R2 is selected from the group comprising a t-butyl group, a tetrahydropyranyl group and a trimethylsilyl group.

16. The chemically amplified photoresist composition of claim 14, wherein the photosensitive polymer mixture comprises a copolymer A polymerized from a monomer of alkoxystyrene or an alkoxystyrene derivative, and a monomer of hydroxystyrene or a hydroxystyrene derivative, and a copolymer B polymerized from a monomer of a (meth) acrylate derivative and a monomer of hydroxystyrene or a hydroxystyrene derivative, and wherein the copolymers A and B are mixed at a ratio of from about 1:9 to 9:1.

17. The chemically amplified photoresist composition of claim 16, wherein the copolymer A is represented by the following chemical formula (CF3), the copolymer B is represented by the following chemical formula (CF4), and each copolymer has a weight average molecular weight of from about 5,000 to 50,000:

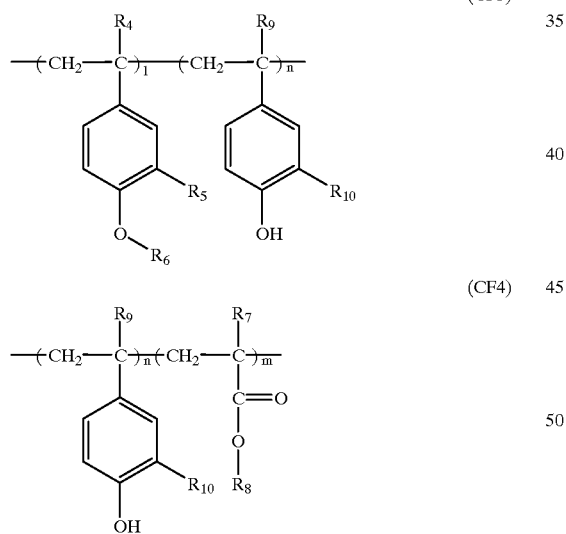

wherein R4, R5, R7, R9 and R10 are each independently selected from the group comprising a hydrogen atom and a methyl group;

R6 is selected from the group comprising alkoxyl-1-ethyl, tetrahydropyranyl, t-butyl and t-butoxycarbonyl;

R8 is selected from the group comprising a t-butyl group and a tetrahydropyranyl group;

l, m and n are integers, n/(n+1) is from about 0.5 to 0.9, and n/(m+n) is from about 0.5 to 0.9.

18. The chemically amplified photoresist composition of claim 17, wherein R6 is a 1-ethoxyethyl group.

19. The chemically amplified photoresist composition of claim 14, wherein the photosensitive polymer mixture comprises a copolymer A polymerized from a monomer of alkoxystyrene or an alkoxystyrene derivative, and a monomer of hydroxystyrene or a hydroxystyrene derivative, and a copolymer B polymerized from a monomer of t-butoxycarbonyloxystyrene or a t-butoxycarbonyloxystyrene derivative, and a monomer of hydroxystyrene or a hydroxystyrene derivative and wherein the copolymers A and B are mixed at a ratio of from about 1:9 to 9:1.

20. The chemically amplified photoresist composition of claim 19, wherein the polymer A is represented by the following chemical formula (CF3), the polymer B is represented by the following chemical formula (CF5), and each polymer has a weight average molecular weight of from about 5,000 to 50,000:

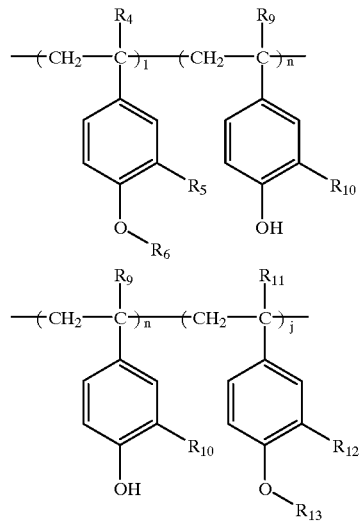

wherein R4, R5, R9, R10, R11 and R12 are each independently one selected from the group comprising a hydrogen atom or a methyl group;

R6 is one selected from the group comprising alkoxyl-1-ethyl, a tetrahydropyranyl, t-butyl and t-butoxycarbonyl;

R13 is a t-butoxycarbonyl group;

j, l and n are integers; n/(l+n) is from about 0.5 to 0.9, and n/(j+n) is from about 0.5 to 0.9.

21. The chemically amplified photoresist composition of claim 20, wherein R6 is a 1-ethoxyethyl group.

22. The chemically amplified photoresist composition of claim 14, wherein the photosensitive acid generator is mixed at a ratio of from about 1 to 15% by weight based on the total weight of the photosensitive polymer mixture.

23. The chemically amplified photoresist composition of claim 14, wherein the photosensitive acid generator is selected from the group comprising triarylsulfonium salts, diaryliodonium salts and sulfonates.

24. The chemically amplified photoresist composition of claim 14, further comprising an organic base of from about 0.01 to 2.0% by weight based on the total weight of the photosensitive polymer mixture.

25. The chemically amplified photoresist composition of claim 24, wherein the organic base is selected from the group comprising triethylamine, triisobutylamine, triisooctylamine, diethanolamine, triethanolamine, and N-methyl pyrrolidone.

* * * * *